United States Patent [19]
Myers et al.

[11] Patent Number: 4,857,738
[45] Date of Patent: Aug. 15, 1989

[54] ABSORPTION MEASUREMENTS OF MATERIALS

[75] Inventors: David W. Myers; Robert G. Ozarski, both of Livermore; Thiloma I. Perera, Sunnyvale; John F. Schipper, Palo Alto; Raul V. Tan, San Jose; Michael P. C. Watts, Portola Valley, all of Calif.

[73] Assignee: General Signal Corporation, Stamford, Conn.

[21] Appl. No.: 135,119

[22] Filed: Dec. 18, 1987

[51] Int. Cl.⁴ .................. G01N 21/21; G01N 21/75
[52] U.S. Cl. ................................. 250/372; 356/370; 436/34
[58] Field of Search ............... 250/372, 341, 358.1; 436/34; 356/432, 370, 445

[56] References Cited
U.S. PATENT DOCUMENTS

| | | | |
|---|---|---|---|
| 3,448,268 | 6/1969 | Proctor | 250/341 |
| 3,524,983 | 8/1970 | Voelz | 250/341 |
| 3,985,447 | 10/1976 | Aspnes | 356/370 |
| 4,555,767 | 11/1985 | Case et al. | 250/341 |

OTHER PUBLICATIONS

Bey, "Optical Film Thickness Monitoring", Rev. Sci. Instru., 42(1), Jan. 1971, pp. 57-60.
Nagendra et al., "Optical Constants of Absorbing Films", Vacuum, 31(3), Mar. 1981, pp. 141-145.
Heavens, "Optical Properties of Thin Solid Films", Butterworth Scientific Publications, London, 1955, pp. 74-80.

Primary Examiner—Carolyn E. Fields
Attorney, Agent, or Firm—Skjerven, Morrill, MacPherson, Franklin & Friel

[57] ABSTRACT

Two methods of determination of the chemical changes induced in a film of material such as photoresist that has been exposed to electromagnetic radiation. Two methods use measurement of polarized light reflected by the film mounted on a substrate to determine a real refractive index or a complex refractive index of the film. Two other methods use measurement of polarized light by the film mounted on a (partly) transparent substrate to determine a real refractive index or a complex refractive index of the film.

19 Claims, 5 Drawing Sheets

ABSORPTION MEASUREMENTS OF MATERIALS

FIELD OF THE INVENTION

This invention relates to determination of the extent of chemical changes induced in a film of a known material by exposure of the film to electromagnetic radiation, using reflection and transmission measurements performed on the film; and, more particularly, it relates to determination of the quantity of light absorbed in a film of photoresist or similar material.

BACKGROUND OF THE INVENTION

Figure 1:
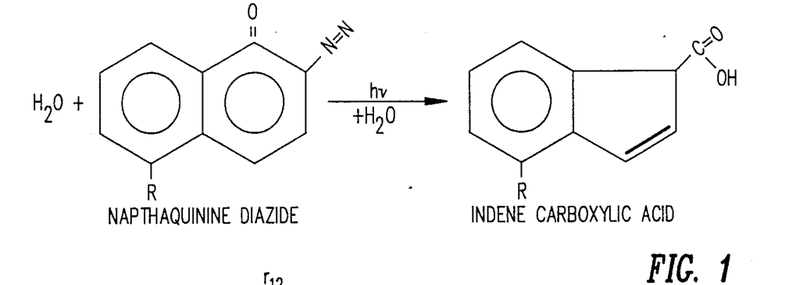
FIG. 1 is a schematic view of the chemical reaction that occurs when a molecule of water, a molecule of napthaquinine diazide, and a photon of wavelength $\lambda = 300$-$450$ nm interact to produce a molecule of indene carboxylic acid.

In order to fully characterize the effect of various photolithography process steps it is important to monitor the effect of each of these process steps on the absorption of the photoresist. Photoresist contains photosensitizer such as napthaquinine diazide (NAQ1), whose chemical structure is shown in FIG. 1. Exposure of photoresist to light, typically of wavelength $\lambda = 300$–$450$ nm, causes the sensitizer to convert to an indene carboxylic acid (ICA), which is soluble in an aqueous base developer.

This arrangement can be monitored using light in the ultraviolet, visible or infrared wavelengths. In the ultraviolet, the change in absorption is due to electronic excitations. The long wavelength electronic excitations are associated with the $\pi$ or double bond electron clouds indicated to FIG. 1. The excitation wavelength is controlled by many factors, with the length of the $\pi$ bond being one of the most significant; the longer the $\pi$ bond, the lower is the energy required for electronic excitation, and hence the longer is the absorption wavelength.

Figure 2:
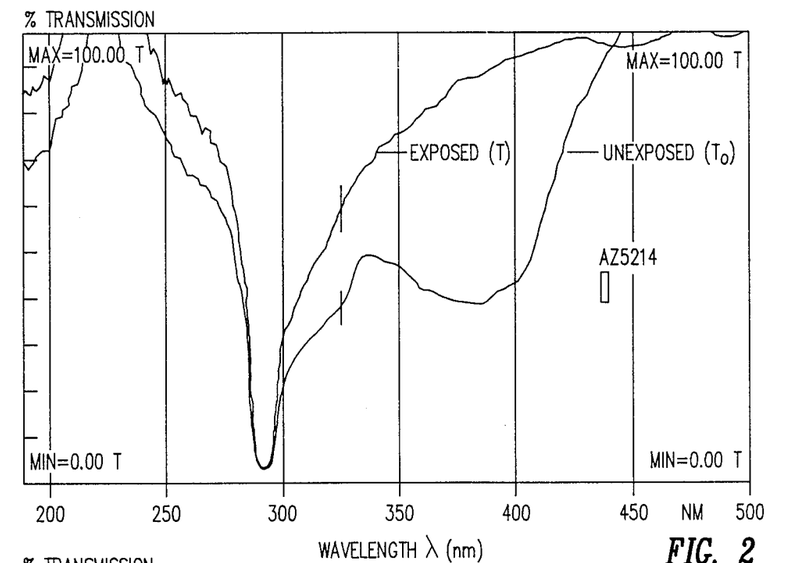
FIGS. 2, 3 and 4 are graphic views comparing the transmission coefficients as a function of wavelength $\lambda$ for unexposed ($T_o$) and substantially fully exposed (T) films of representative photoresist materials AZ5214, AZ4110 and AZ1370, respectively.
Figure 3:
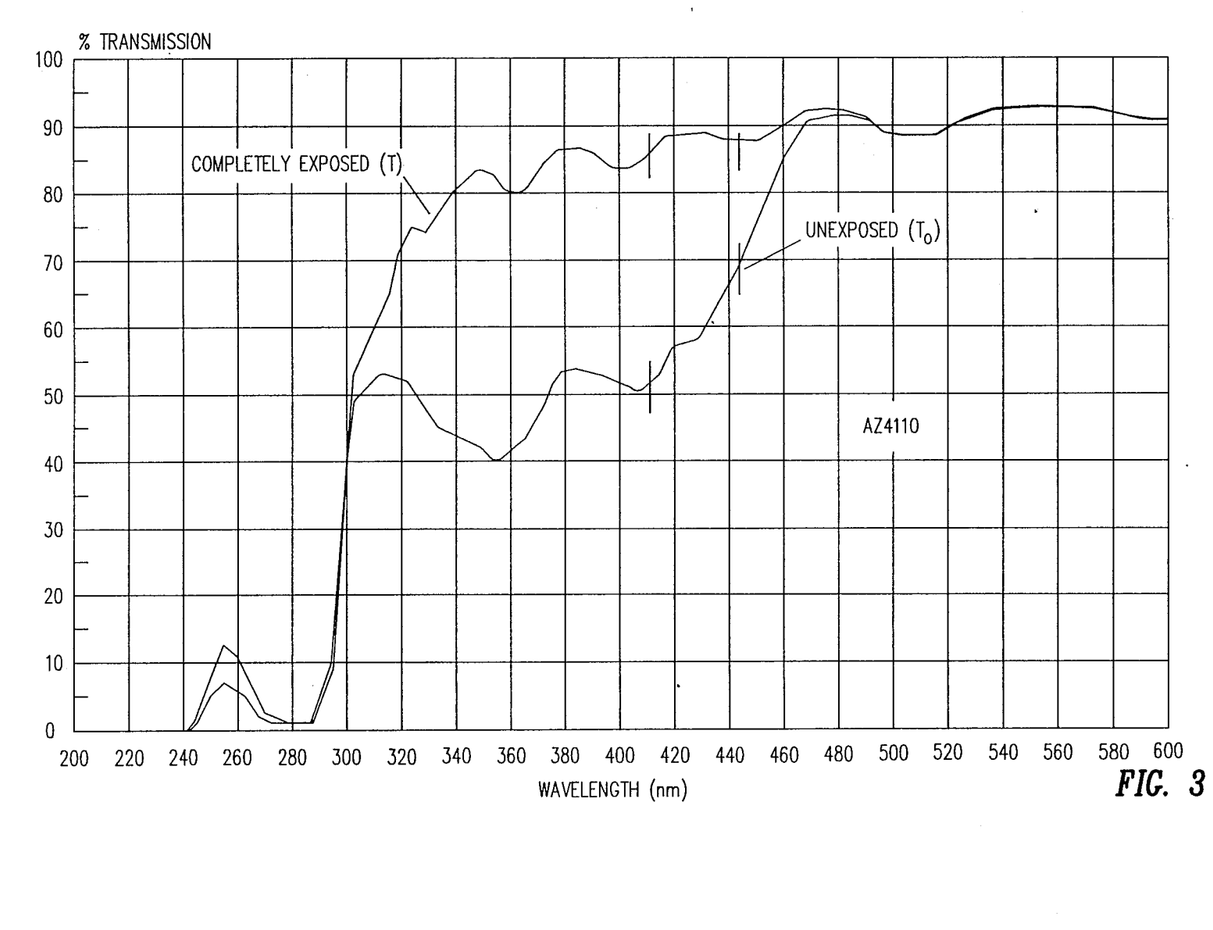
Figure 4:
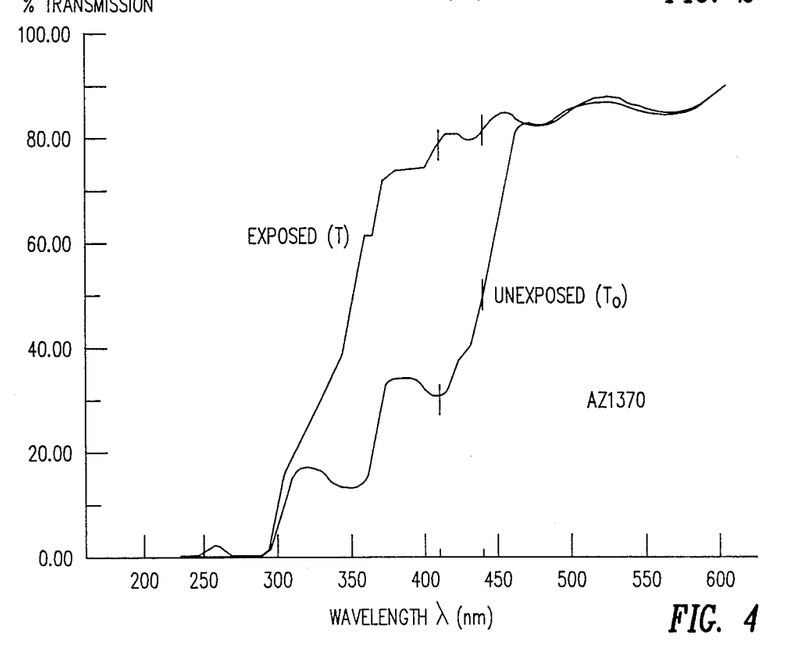

The bond lengths in NAQ1 are as large as or larger than the corresponding bond lengths in ICA; hence the NAQ1 has longer wavelength absorption than the ICA. This is shown in the comparison of transmission coefficients in the UV and low visible wavelength regions for three different photoresist materials, AZ5214, A4110 and AZ1370 in FIGS. 2, 3 and 4, respectively. Transmission coefficient differences between exposed and unexposed photoresist material are significant between $\lambda \approx 300$ nm and $\lambda \approx 450$ nm for each material. The photoresist becomes more transparent upon exposure at the usual exposure wavelengths of $\lambda = 300$–$450$ nm. A theoretical equation relating transmission coefficient before exposure ($T_o$) and after exposure (T) to a dose D (Joules/cm$^2$) of light at a prescribed irradiation wavelength $\lambda$ is $$T = [1 + (1/T_o - 1)e^{-CD}]^{-1}$$

where the constant $C \approx 0.012$–$0.015$ cm$^2$/Joule and will vary with $\lambda$ and with the photoresist material. As a result, the change in visible/uv absorption of the photoresist material can be used to determine the degree of exposure.

The reaction or conversion of the photoresist component can also be monitored in the infrared wavelengths. The infrared radiation is absorbed by bond vibrations. The —N≡N bond of the diazo side group has a vibration at 2100 cm$^{-1}$, isolated from all other bond vibrations. As the NAQ1 is exposed, the absorption due to —N≡N vibrations is reduced in substantially the same proportion as the number of —N≡N bonds is reduced by conversion.

SUMMARY OF THE INVENTION

One object of the invention is to provide a method of determining the fraction of photosensitizer component in a film of photoresist material that has been converted by exposure to light of appropriate irradiation wavelength, by use of radiation absorption measurements using light reflection and/or light transmission techniques.

Another object is to provide this determination of the fractional conversion by exposure to light of photoresist material contained in a film, where the film is mounted on one of its faces on a substrate that has known material properties and thickness.

Other objects of the invention, and advantages thereof, will become clear by reference to the detailed description and the accompanying drawings.

In accordance with this invention, a method for achieving the foregoing and other objects is provided that in one embodiment comprises: providing a substantially planar film of thickness $t_2$ and known refractive index $n_2(\lambda)$ at a predetermined wavelength $\lambda$; mounting the film on a substrate with known refractive index $n_3(\lambda)$ at the wavelength $\lambda$; providing a source of light of wavelength $\lambda$; positioning the film-substrate combination so that the film lies between at least a portion of the substrate and the light source; propagating a light beam from the source toward the exposed face of thhe film at a predetermined incidence angle $\theta_1$ ($\theta \leq \theta_1 < \pi/2$); allowing the incident light beam to be reflected at the exposed face of the film and at the film-substrate interface and measuring the total reflectivity $R = I_r/I_o$, where $I_o$ and $I_r$ are of the incident intensity and total reflected intensity of the light, respectively; determining the absorption a of the film material substantially from the expressions $$1 - a = e^{-\alpha_2 L_2} = \{[-r_{12}(1-R)\cos\beta_2 \pm$$
$$[r_{12}^2(1-R)^2\cos^2\beta_2 + (R-r_{12})^2(1-Rr_{12})^2]^{\frac{1}{2}}]/r_{23}(1-Rr_{12})^2\},$$

$$L_2 = 2t_2\sec\theta_2,$$

$$\beta_2 = \frac{4\pi n_2 t_2}{\lambda}\cos\theta_2,$$

$$\cos\theta_2 = [1 - \sin^2\theta_1/n_2^2]^{\frac{1}{2}},$$

$$\cos\theta_3 = [1 - \sin^2\theta_1/n_3^2]^{\frac{1}{2}},$$

where $\alpha_2$ is a linear absorption parameter ($\mu m^{-1}$) for the film material, $r_{12} = r_{12}(\theta_1, \theta_2; k)$ is the amplitude reflection coefficient for the (air or vacuum)-film interface, $r_{23} = r_{23}(\theta_2, \theta_3; k)$ is the amplitude reflection coefficient for the film-substrate interface at initial incidence angle $\theta_1$, and k($=$p for p-polarization waves and $=$s for s-polarization waves) is the polarization index for the incident beam. A variation of this embodiment uses the theoretically exact expressions for R and the amplitude reflection and transmission coefficients $r_{ij}$ and $t_{ij}$ set forth in Eqs. (32)–(75).

In a second embodiment, a method is provided that comprises: providing a substantially planar film of thickness $t_2$ and known refractive index $n_2(\lambda)$ at a predetermined wavelength $\lambda$; mounting the film on a substrate of thickness $t_3$ with known refractive index $n_3(\lambda)$ at the wavelength $\lambda$ and known linear absorption coefficient $\alpha_3$; providing a source of light of wavelength $\lambda$; positioning the film-substrate combination so that the film lies between at least a portion of the substrate and the light source; propagating a light beam from the source toward the exposed face of the film at a predetermined incidence angle $\theta_1$ ($\theta \leq \theta_1 < \pi/2$); allowing the incident light beam to be transmitted through the film and substrate and measuring the total transmission $T = I_t/I_o$, where $I_o$ and $I_t$ are the incident intensity and total transmitted intensity of the light, respectively; determining the absorption a of the film material substantially from the expressions $$(1 - a)^2 = \{(r_{21}r_{23}\cos\beta_2 + 1/TF) \pm [(r_{21}r_{23}\cos\beta_2 + 1/TF)^2 - r_{21}^2 r_{23}^2]^{\frac{1}{2}}\}/r_{21}^2 r_{31}^2,$$

$$\frac{F}{2} = \frac{e^{2a_3L_3} - 2r_{31}r_{32}\cos\beta_3 + r_{31}^2 r_{32}^2 e^{-2a_3L}}{(1 - r_{12}^2)(1 - r_{23}^2)(1 - r_{31}^2)},$$

$$L_2 = 2t_2 \sec\theta_2,$$

$$L_3 = 2t_3 \sec\theta_3,$$

$$\beta_2 = \frac{4\pi n_2 t_2}{\lambda} \cos\theta_2,$$

$$\beta_3 = \frac{4\pi n_3 t_3}{\lambda} \cos\theta_3,$$

$$\cos\theta_2 = [1 - \sin^2\theta_1/n_2^2]^{\frac{1}{2}},$$

$$\cos\theta_3 = [1 - \sin^2\theta_1/n_3^2]^{\frac{1}{2}},$$

where $r_{12}(\theta_1, \theta_2; k) = r_{21}$ $r_{23} = r_{23}(\theta_2, \theta_3; k)$ and $r_{31} = r_{31}(\theta_3, \theta_1; k)$, are, respectively, the amplitude reflection coefficients appropriate for the vacuum-film interface at incidence angle $\theta_1$ in the vacuum the film-substrate interface at incidence angle $\theta_2$ in the film, and the substrate-vacuum interface at incidence angle $\theta_3$ in the substrate, and $k(=p$ or $s)$ is the polarization index for the incident beam. A variation of this embodiment uses the theoretically exact expressions for T and the complex amplitude reflection and transmission coefficients $r_{ij}$ and $t_{ij}$ set forth in Eqs. (32)-(68) and (91)-(98).

DESCRIPTION OF PREFERRED EMBODIMENTS

To measure the change in absorption of the photoresist, a variety of methods can be implemented. The most important requirement is that the measurement be made at an appropriate wavelength where molecular excitation occurs, as discussed above. For the diazide-based positive photoresists, the wavelengths of interest are approximately $\lambda = 4.7$ $\mu$M for monitoring changes in the vibrational absorption and $\lambda = 300$-$450$ nm for monitoring changes in atomic excitation absorption. Also of importance to the measurement of the absorption of photoresists is the amount of energy deposited by the measurement method into the photoresist; the measurement technique must not significantly expose the photoresist during the time of the measurement. The methods disclosed here monitor either reflected radiation or transmitted radiation in determining the quantity of light previously absorbed, or the fraction of the photosensitive component previously converted by a given radiation dose.

Absorption measurements of the photoresist layer coated on a substrate can be made by measuring the amount of incident light reflected from the sample. In this method, the incident light will travel through the thin film layer, reflect once from the substrate, pass through the layer a second time, either be transmitted at the film-vacuum interface, or be reflected many times within the film and then be transmitted, and be measured. By knowing the incident intensity $I_o$ and measuring the reflected intensity $I_r$, the absorption a of the thin film layer may be approximated by the following:

$$1 - a = e^{-aL} = \frac{1}{2}(I/I_o - R_{12})|R_{23}|^{\frac{1}{2}}(1 - R_{12}) \qquad (1)$$

$\alpha$ = linear absorption coefficient in the film (cm$^{-1}$),
L = round trip optical path length in film,
$R_{12}$ = intensity reflection coefficient at (air/vacuum)−film interface,
$R_{23}$ = intensity reflection coefficient at film-substrate interface.

Figure 5:
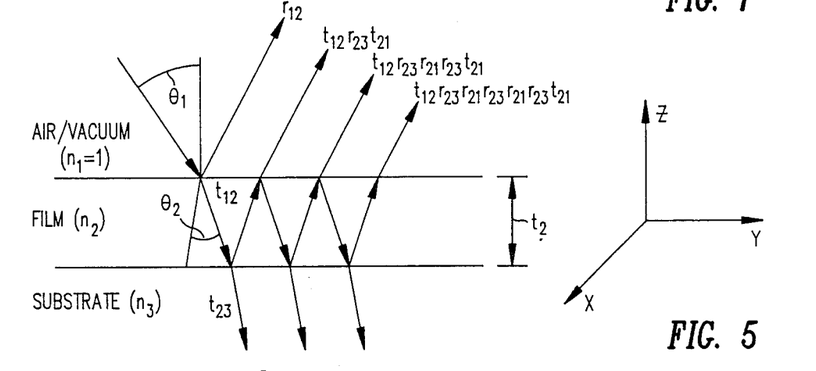
FIG. 5 is a schematic view of the film-substrate combination and the various reflected and transmitted amplitude components that contribute to measured reflectivity R.

The configuration in which these measurements are made is shown schematically in FIG. 5. The incident light of wavelength $\lambda$ approaches the exposed face of the film at incidence angle $\theta_1$, and is partly reflected at this face. The unreflected remainder of the light is transmitted into the film at a refraction angle $\theta_2$ and proceeds to the film-substrate interface, where a portion is reflected and the remaining portion is transmitted into the substrate material at a refraction angle $\theta_3$. The refraction angles $\theta_2$ and $\theta_3$ are determined as usual from the incidence angle $\theta_1$ by the relations $$n_1(\lambda) \sin\theta_1 = n_2(\lambda) \sin\theta_2 = n_3(\lambda) \sin\theta_3, \qquad (2)$$

where $n_1(\lambda)$, $n_2(\lambda)$ and $n_3(\lambda)$ are the wavelength-dependent indices of refraction in material #1 (air or vacuum, $n_1=1$), material #2 (film) and material #3 (substrate), respectively. The amplitude reflection coefficients $r_{12}$ and $r_{23}$ for incident light that is linearly polarized in the plane of incidence ("p-polarization wave", denoted by subscript p) or linearly polarized perpendicular to the plane of incidence ("s-polarization wave", denoted by subscript s) are given by $$r_{12,p}(\theta_1,\theta_2) = \frac{n_2\cos\theta_1 - n_1\cos\theta_2}{n_2\cos\theta_1 + n_1\cos\theta_2}, \quad (3)$$

$$r_{12,s}(\theta_1,\theta_2) = \frac{n_1\cos\theta_1 - n_2\cos\theta_2}{n_1\cos\theta_1 + n_2\cos\theta_2}, \quad (4)$$

$$r_{23,p}(\theta_2,\theta_3) = \frac{n_3\cos\theta_2 - n_2\cos\theta_3}{n_2\cos\theta_3 + n_2\cos\theta_3}, \quad (5)$$

$$r_{23,s}(\theta_2,\theta_3) = \frac{n_2\cos\theta_2 - n_3\cos\theta_3}{n_2\cos\theta_2 + n_3\cos\theta_3}. \quad (6)$$

With the polarization index k included here (k=p and k=s corresponding to p-polarization and s-polarization, respectively), one can write $r_{ij}=r_{ij,k}(\theta_i,\theta_j)$.

If material absorption and the multiple reflections and associated phase shifts at the interfaces, as indicated in FIG. 5, are taken into account, the total intensity ratio or reflectivity R of light reflected from the film/substrate combination may be found by an extension of the reflectivity calculations presented in M. Born and E. Wolf, *Principles of Optics* Pergamon Press, Fifth Edition, 1975, pp. 36–44 and 59–63. The reflectivity R is found to be $$R = \frac{I_r}{I_o} = \frac{r_{12}^2 + r_{23}^2 e^{-2\alpha L} + 2r_{12}r_{23}e^{-\alpha L}\cos\beta}{1 + r_{12}^2 r_{23}^2 e^{-2\alpha L} + 2r_{12}r_{23}e^{-\alpha L}\cos\beta} \quad (7)$$

$\beta = (4\pi/\lambda)n_2 t \cos\theta_2$,
t = film thickness,
$\alpha$ = linear absorption coefficient (cm$^{-1}$),
L = round trip path length in film = $2t \sec\theta_2$,
$I_o$ = incident light intensity
$I_r$ = reflected light intensity (all waves).

This assumes that any light transmitted into the substrate material does not return to the film-substrate interface.

If the incident light is partially or fully polarized, the reflected amplitude R must be computed separately for the parallel and perpendicular polarization E field amplitudes $E_{o,p}$ and $E_{o,s}$ and associated amplitude reflection coefficients, where $E_o^2/2 = I_o$ is the incident intensity of the light. The expression for R may be inverted to yield the absorption $a = 1 - e^{-aL}$ with $$e^{-\alpha L} = \frac{1/r_{23}}{1-Rr_{12}^2}[-r_{12}(1-R)\cos\beta \pm \quad (8)$$

$$[r_{12}^2(1-R)^2\cos^2\beta + (R-r_{12}^2)(1-Rr_{12}^2)]^{\frac{1}{2}}],$$

from which the linear absorption coefficient $\alpha$ may be determined if L is known accurately. In particular, for p-polarized light incident at the Brewster angle $$\theta_1 = \theta_{1B} = \tan^{-1}(n_2/n_1) \quad (9)$$

one easily verifies from Equations (1), (2) and (3) that $r_{12,p}(\theta_{1B})=0$ and that $$e^{-\alpha L} = [R/r_{23,p}^2]^{\frac{1}{2}}, \quad (10)$$

if R and/or $r_{23,p}$ do not vanish. One can verify in a straightforward manner that $r_{23,p}$, given by Equation (5), does not vanish for $\theta_1 = \theta_{1B}$ unless $n_3=1$ (no substrate) or $n_3=n_2$ (substrate identical with film).

The Equations (7) and (8) take full account of film interference effects, phase differences of different reflected components, and absorption within the film. The use of incidence angle $\theta_1=\theta_{1B}$ simplifies the absorption determination further by removing the effect of phase differences on the absorption a. One subtle difficulty occurs here, however: as absorption (conversion) increases, the index $n_2$ may change so that the Brewster angle $\theta_{1B}$ also changes. This effect may be accounted for by changing the incident beam angle. The incident light should be p-polarized and well collimated to avoid or minimize any reflection from the exposed face of the film at $\theta_1=\theta_{1B}$.

In order to make measurements of reflectivity R accurate to 1 part in 100 the divergence of the incident beam must be less than approximately 3 milliradians. This required beam divergence can be met by using a laser as the source. Incandescent or arc sources could also be used, but the requirement of minimal divergence requires either a high brightness source or a fairly large measurement area. Laser sources in the wavelength range 300–450 nm are limited to a few expensive choices, except for a HeCd laser operating at $\lambda=442$ nm or $\lambda=325$ nm. An operating measurement system has been made using the above-described Brewster's angle measurement technique and a HeCd laser source.

Because of beam divergence the Brewster relation $\theta_1=\theta_{1B}$ is not satisfied for all light rays that comprise an incident beam, the p-polarization reflection coefficient $r_{12,p}(\theta_1)$ will be small but will not vanish for certain rays; and the simple form of Eq. (10) will not be satisfied for such rays. From Eq. (8), for small $r_{12}$ one finds the approximation $$e^{-\alpha L} = 1/r_{23}\{R^{\frac{1}{2}}-(1-R)\cos\beta r_{12}-1/2R^{-\frac{1}{2}}<(1+R^2)-(1-R)^2\cos^2\beta>r_{12}^2+O(r_{12}^4)\}, \quad (11)$$

where $O(r^m)$ denotes a function $f(r)$ for which $\text{Lim}_{r\to o}f(r)/r^m$ exists and is finite.

Using Eq. (11) one can obtain an approximate bound on the fractional error for the absorption $a=1-e^{-\alpha L}$ measured at or near $\theta_1=\theta_{1B}$ $$\left|\frac{e^{-\alpha L}}{R^{\frac{1}{2}}|r_{23}|} - 1\right| \leq \left|\frac{1-R}{R^{\frac{1}{2}}}\cos\beta\right||r_{12}| + \quad (12)$$

$$\frac{1}{2R}\left|(1+R^2)-(1-R)^2\cos^2\beta\right|r_{12}^2 + O(r_{12}^4),$$

where $r_{12}=r_{12,p}$ is the p-wave amplitude reflection coefficient at or near the Brewster angle $\theta_{1B}$ for the vacuum-film interface. At $\theta_1=\theta_{1B}$, the left hand quantity in Eq. (12) should vanish; for $\theta_1\approx\theta_{1B}$ but $\theta_1\neq\theta_{1B}$, Eq. (12) provides a bound on the fractional error involved in using $e^{-\alpha L}=[R/r_{23}^2]^{\frac{1}{2}}$ As a numerical example, consider a film/substrate combination with the following parameters:
$\lambda=0.442$ μm, $n_2(\lambda) = 1.64$,
$n_3(\lambda) = 4.774$,
$\alpha = 0.3 \ \mu m^{-1}$,
$t = 1 \ \mu m$,
$\theta_1 \doteq \theta_B = 58.6270° = \pi/2 - \theta_2$
$R = 0.04594$
$r_{23} = 0.4328$ at $\theta_1 = \theta_B$ Equation (12) may be written as $$\left| \frac{e^{-\alpha L}}{R^{\frac{1}{2}} |r_{23}|} - 1 \right| \leq 2.288 \ |r_{12}| + 8.291 \ r_{12}^2 + 0(r_{12}^4) \quad (12')$$

with $\sqrt{R}/|r_{23}| = 0.4953$ here. For a light beam whose incidence anngle differs from $\theta_B$ by 3 milliradians ($\Delta\theta = 0.1719°$), $r_{12,p} = -0.002119$ and the error bound in Eq. (12') becomes $$\left| \frac{e^{-\alpha L}}{R^{\frac{1}{2}} |r_{23}|} - 1 \right| \leq .00489.$$

This is a fractional error of about 0.5 percent.

One troublesome feature in the use of Eq. (7) is that the value of R can vary rapidly as $$\beta = \frac{4\pi n_2 t}{\lambda} \cos\theta_2$$

changes, with R attaining the extremum values $$R_{max} = \left( \frac{r_{12} + r_{23}e^{-\alpha L}}{1 + r_{12}r_{23}e^{-\alpha L}} \right)^2 \quad (13a)$$

$$R_{min} = \left( \frac{r_{12} - r_{23}e^{-\alpha L}}{1 - r_{12}r_{23}e^{-\alpha L}} \right)^2 \quad (13b)$$

at $\beta = 2n\pi$ and $\beta = (2n+1)\pi$ (n = 0, 1, 2, . . . ), respectively, if $r_{12}r_{23} > 0$; and with the $R_{min}$ and $R_{max}$ expressions exchanged for $r_{12}r_{23} < 0$. In particular, R can vanish if $r_{12} = r_{23}e^{-\alpha L}$. For the normal incidence situation ($\theta_1 = \theta_2 = \theta_3 = 0$), this requires that $$n_3 = n_2 \frac{n_2 - z}{1 - n_2 z} \quad (14a)$$

where $$z = \frac{1 - e^{-\alpha L}}{1 + e^{-\alpha L}} \ (0 < z < 1)$$

$$e^{-\alpha L} = \frac{n_3 - 1 - (n_3/n_2 - n_2)}{n_3 - 1 + (n_3/n_2 - n_2)}.$$

In particular, for real substrate materials with $n_3 \geq 1$ Eqs. (14a) and (14b) require that $n_3 > n_2^2$ so that R cannot vanish for normal incidence (at any thickness) if $n_3 \leq n_2$. This would be true, for examle, where the substrate is glass with $n_3(\lambda_{visible}) \approx 1.5$ and the film material refractive index is $n_2(\lambda_{visible}) \approx 1.64$. However, if $n_2 < (n_3)^{\frac{1}{2}}$ one thickness t may be found for which $r_{12,p} - r_{23,p}e^{-\alpha L} = 0$ at normal incidence; this is also true for small angles $\theta_1$. As an example, with the same parameter choices
$\lambda = 0.442 \ \mu m$,
$n_2 = 1.64$,
$n_3 = 4.774$,
$\theta_1 = \theta_2 = \theta_3 = 0$,
Eq. (14b) yields $$a = 1 - e^{-\alpha L} = 0.5039$$

from which round trip path length $2L = 2t$ can be determined if $\alpha$ is known.

It is not necessary to be at Brewster's angle, with no p-polarization wave reflections from the (1,2) interface, in order to measure the absorption. If the thickness is known, the modulations on the reflected light signal due to the thin film interference can be calculated. The difference between the calculated signal with no absorption and the measure signal with absorption, allows the absorption to be determined. However, depending on the angle and thickness of the sample it is possible for the measured signal to be at an interference minima, which can be zero or a value that is too small to accurately measure for practical detection circuits. This condition can be avoided by using two measurement beams reflected from the interface, both of the same wavelength but at two angles that lie on different sides of Brewster's angle. Because the phase of the reflected light from the (1,2) interface abruptly changes from 0° to 180° at Brewster's angle the two reflected from 0° to 180° at Brewster's angle the two reflected signals will be 180° out of phase with each other. Therefore, the modulation of each of the two beams produced by thin film interference will be out of phase with each other. The result is that, if the thickness and angle on a particular film produces a modulation minima on one reflected signal beam, the other reflected signal beam will be at a maxima. This ensures that there will always be at least one signal to determine absorption that is not attenuated by interference to a value that is too low to measure.

Figure 6:
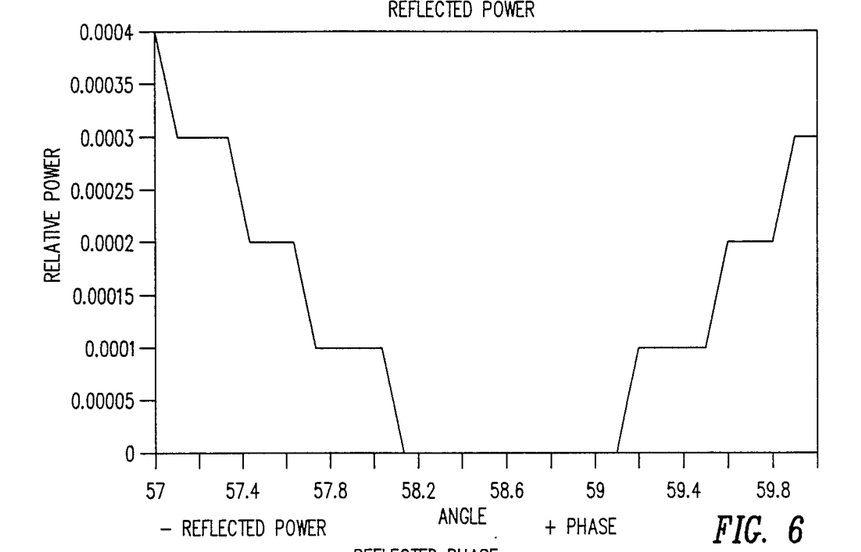
FIGS. 6 and 7 are graphs of calculated reflected power fraction RP and associated phase angle, respectively, for an incident wave near the conventional Brewster's angle $\theta_1 = \theta_{1B} = \tan^{-1}(n_2/n_1)$ ($\approx 58.63+$ for a photoresist film).
Figure 7:
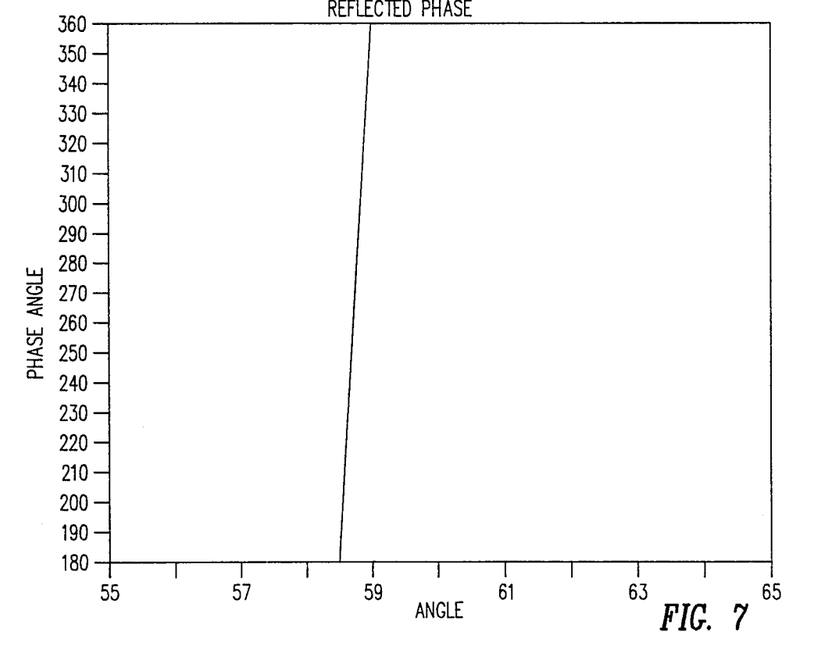
Figure 8:
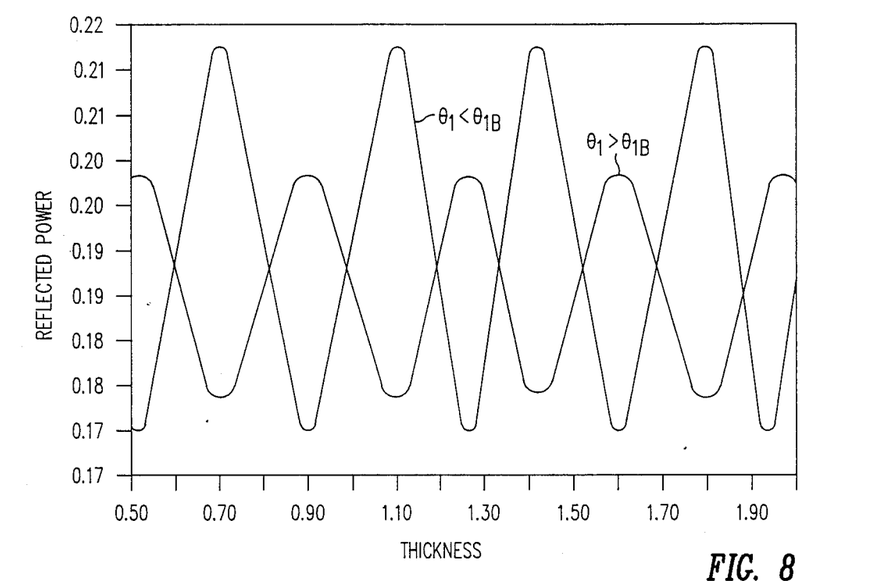
FIG. 8 is a graph of reflected power at two angles slightly greater than and slightly less than Brewster's angle $\theta_1 = \theta_{1B}$, as a function of film thickness.

FIGS. 6 and 7 are graphs of calculated reflected power and phase angle as functions of incidence angle $\theta_1$ near Brewster's angle; and FIG. 8 is a graph of the signal from two beams at angles greater than and less than Brewster's angle, as a function of film thickness.

The preceding discussion has used the physical optical formulation appropriate for a non-absorbing medium to derive Eqs. (2)–(7) for the amplitude reflection coefficients at the vacuum-film interface and the film-substrate interface and the associated reflectivity R at the vacuum-film interface. Although these expressions may afford good approximations, the formulations are not theoretically correct as the film and substrate materials are or may be metal-like; this requires a more elaborate analysis. An absorbing medium (metal-like) has an effective current density vector $\underline{J}$ that is assumed here to be proportional to the electric field strength vector $\underline{E}$: $\underline{J} = \sigma\underline{E}$ for an isotropic, linear medium, where $\sigma$ is the electrical conductivity of the medium. This analysis is best formulated beginning with the well known Maxwell equations relating electric field strength $\underline{E}$, magnetic field strength $\underline{H}$, electric displacement $\underline{D} = \epsilon\underline{E}$, magnetic flux $\underline{B} = \mu\underline{H}$, charge density $\rho$ and current density $\underline{J}$, viz.

$$\underline{\nabla} \wedge \underline{E} = -\frac{1}{c} \frac{\partial}{\partial t} \underline{B}, \ \underline{\nabla} \cdot \underline{D} = 4\pi\rho,$$

$$\underline{\nabla} \wedge \underline{H} = \frac{1}{c} \frac{\partial}{\partial t} \underline{E} + \frac{4\pi}{c} \underline{J}, \ \underline{\nabla} \cdot \underline{B} = 0,$$

-continued $$\underline{J} = \sigma \underline{E}, \underline{D} = \epsilon \underline{E}, \underline{B} = \mu \underline{H},$$

$\epsilon$ = dielectric permittivity constant,
$\mu$ = magnetic permittivity constant.

In the usual manner one can obtain the wave propagation equations for such a medium with $\rho = 0$ $$\left( \underline{\nabla}^2 - \frac{\epsilon\mu}{c^2} \frac{\partial^2}{\partial t^2} - \frac{4\pi\sigma\mu}{c^2} \frac{\partial}{\partial t} \right)(\underline{E} \text{ or } \underline{H}) = \underline{0} \quad (15)$$

For the isotropic medium (vacuum or film or substrate) considered here the plane wave solution of Eqs. (15) is $$\underline{E} = \underline{E}_o \exp[i(\underline{q} \cdot \underline{r} - \omega t)](i^2 = -1), \quad (16)$$

$$\underline{H} = \underline{H}_o \exp[i(\underline{q} \cdot \underline{r} - \omega t)] \quad (17)$$

$$q^2 = \left[ \frac{\omega}{c}(n_r + in_i) \right]^2 = \frac{\omega^2}{c^2}\left( \mu\epsilon + i\frac{4\pi\sigma\mu}{\omega} \right), \quad (18)$$

$$n_r^2 = \frac{1}{2}(\mu\epsilon + [(\mu\epsilon)^2 + (4\pi\sigma\mu/\omega)^2]^{\frac{1}{2}}) \approx \quad (19)$$

$$\mu\epsilon\left[ 1 + \left( \frac{2\pi\sigma}{\epsilon\omega} \right)^2 \right] \text{if } \frac{\pi\sigma}{\epsilon\omega} << 1,$$

$$n_i^2 = \frac{1}{2}(-\mu\epsilon + [(\mu\epsilon)^2 + (4\pi\sigma\mu/\omega)^2]^{\frac{1}{2}}) \approx \quad (20)$$

$$\frac{\mu}{\epsilon}\left( \frac{2\pi\sigma}{\epsilon\omega} \right)^2 \text{if } \frac{\pi\sigma}{\epsilon\omega} << 1.$$

Here $n_r$ and $n_i$ are, respectively, the real an imaginary components of the refractive index of the medium. For a non-absorbing medium, $\sigma = 0$ and $n_r + in_i$ reduces to the usual (real) refractive index for the medium (e.g., $n_1$ for the vacuum) for an absorbing medium $$\underline{E} = \underline{E}_o \exp\left[ i\left( \frac{\omega}{c} n_r \hat{\underline{k}} \cdot \underline{r} - \omega t \right) \right] \exp\left[ -\frac{\omega}{c} n_i \hat{\underline{k}} \cdot \underline{r} \right], \quad (21)$$

$\hat{\underline{k}}$ = unit vector in wave propagation direction; and for $\hat{\underline{k}} \cdot \underline{r} = r$ the quantity $$\alpha = \frac{2\omega}{c} n_i = \frac{4\pi}{\lambda} n_i \quad (22)$$

is identified with the linear absorption coefficient (expressed in units of $cm^{-1}$) for the medium: $|\underline{E}|^2 \propto \exp(-\alpha r)$ for a wave propagating radially outward.

At an interface between medium 1 and medium 2, the Maxwell equations in volume or surface integral form may be manipulated to yield the following boundary conditions across the interface, in the absence of surface current and surface charge density:

tangential component of $E$ continuous. (23)
normal component of $(\epsilon + i\sigma/\omega)E$ continuous.
tangential component of $H$ continuous.
normal component of $H$ continuous.

Figure 10:
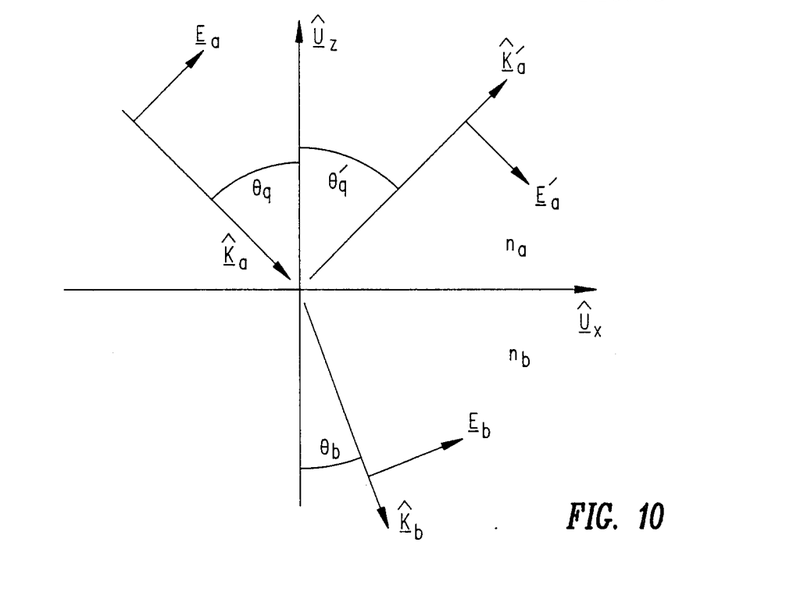
FIG. 10 is a schematic view of the orientation of the electric field vectors E and associated wave propagation vectors K assumed for the incident, reflected and refracted waves analyzed for complex or absorbing media.

The last two of Equations (23) are implied by the first two. Consider the situation illustrated in FIG. 10 where a p-polarized electromagnetic wave ($\underline{E}_1$, $\underline{H}_1$, $\hat{\underline{k}}_1$) in a general medium no. 1 is incident on the interface between medium a and medium b. At the (a,b) interface, with the $\underline{E}$ and $\underline{H}$ vectors in each medium expressed as in Eqs. (16) and (17), matching the amplitudes of $\underline{E}$ and of $\underline{H}$ along the (a,b) interface and using the boundary conditions (23) at the (1,2) interface, one obtains the following relations between the components of the incident field vectors $\underline{E}_a$ and $\underline{H}_a$ (specified initially), the reflected field vectors $\underline{E}_a'$ and $\underline{H}_a'$, and the transmitted field vectors $\underline{E}_b$ and $\underline{H}_b$ (applicable to the wave propagating in medium b):

$$q_a = \frac{\omega}{c}(n_{ar} + in_{ai}), \quad \theta_a = \theta_{ar} + i\theta_{ai}, \quad (24)$$

$$q_a' = \frac{\omega}{c}(n_{ar}' + in_{ai}'), \quad \theta_a' = \theta_a,$$

$$q_b = \frac{\omega}{c}(n_{br} + in_{bi}), \quad \theta_b = \theta_{br} + i\theta_{bi},$$

$$q_a \sin\theta_a = q_a' \sin\theta_a' = q_b \sin\theta_b,$$

$$\underline{E}_s = (\underline{E}_{so,r} + i\underline{E}_{so,i}) \exp\left[ i\left( \frac{\omega}{c} n_{sr}\hat{\underline{k}} \cdot \underline{r} - \omega t \right) - \quad (25) \right.$$

$$\left. \frac{\omega}{c} n_{si}\hat{\underline{k}} \cdot \underline{r} \right] (s = a, a', b)$$

$$\underline{H}_s = (\underline{H}_{so,r} + i\underline{H}_{so,i}) \exp\left[ i\left( \frac{\omega}{c} n_{sr}\hat{\underline{k}} \cdot \underline{r} - \omega t \right) - \quad (26) \right.$$

$$\left. \frac{\omega}{c} n_{si}\hat{\underline{k}} \cdot \underline{r} \right]$$

$$(E_{ao,r} + E_{ao,r}')\cos\theta_{ar}\cosh\theta_{ai} + (E_{ao,i} + E_{ao,i}')\sin\theta_{ai} = = \quad (27)$$

$$E_{bo,r}\cos\theta_{br}\cosh\theta_{bi} + E_{bo,i}\sin\theta_{br}\sinh\theta_{bi}.$$

$$-(E_{ao,r} + E_{ao,r}')\sin\theta_{ar}\sinh\theta_{ai} + \quad (28)$$

$$(E_{ao,i} + E_{ao,i}')\cos\theta_{ar}\cosh\theta_{ai} = =$$

$$-E_{bo,r}\sin\theta_{br}\sinh\theta_{bi} + E_{bo,i}\cos\theta_{br}\cosh\theta_{bi}.$$

$$(E_{ao,r} - E_{ao,r}')\left[ \epsilon_a\sin\theta_{ar}\cosh\theta_{ai} - \frac{4\pi\sigma_a}{\omega}\cos\theta_{ar}\sinh\theta_{ai} \right] - \quad (29)$$

$$(E_{ao,i} - E_{ao,i}')\left[ \epsilon_a\cos\theta_{ar}\sinh\theta_a + \frac{4\pi\sigma_a}{\omega}\sin\theta_{ar}\cosh\theta_{ai} \right] =$$

$$E_{bo,r}\left[ \epsilon_b\sin\theta_{br}\cosh\theta_{bi} - \frac{4\pi\sigma_b}{\omega}\cos\theta_{br}\sinh\theta_{bi} \right] -$$

$$E_{bo,i}\left[ \epsilon_b\cos\theta_{br}\sinh\theta_{bi} - \frac{4\pi\sigma_b}{\omega}\sin\theta_{br}\cosh\theta_{bi} \right]$$

-continued $$(E_{ao,r} - E'_{ao,r})\left[\epsilon_a\cos\theta_{ar}\sinh\theta_{ai} + \frac{4\pi\sigma_a}{\omega}\sin\theta_{ar}\cosh\theta_{ai}\right] + \quad (30)$$

$$(E_{ao,i} - E'_{ao,i})\left[\epsilon_a\sin\theta_{ar}\cosh\theta_a - \frac{4\pi\sigma_a}{\omega}\cos\theta_{ar}\sinh\theta_{ai}\right] =$$

$$E_{bo,r}\left[\epsilon_b\cos\theta_{br}\sinh\theta_{bi} - \frac{4\pi\sigma_b}{\omega}\sin\theta_{br}\cosh\theta_b i\right] +$$

$$E_{bo,i}\left[\epsilon_b\sin\theta_{br}\cosh\theta_{bi} + \frac{4\pi\sigma_b}{\omega}\cos\theta_{br}\sinh\theta_b i\right]$$

For the interface choice (a,b)=(1,2), the initial medium of propagation here is non-absorbing and $\sigma_a = \alpha_1 = 0$ and $\theta_1$ and $\underline{E}_{10}$ are real $(\theta_{1i}=0=E_{10,i})$ although $E_{10,i}'$ may be non-zero. For the other interface choices of interest, namely $(a,b) = (2,1), (2,3), 3,2)$ or $(3,1)$, no additional simplifying assumptions may be made. The angles $\theta_2$ and $\theta_3$ are generally complex, as are the amplitudes $E_{20}$ and $E_{30}$. Where the (1,2), (2,3) and (3,1) interfaces are flat and parallel Eqs. (24) relating the angles $\theta_1$, $\theta_2$ and $\theta_3$ become $$n_{1r}\sin\theta_1 = (n_{2r} + in_{2i})(\sin\theta_{2r}\cosh\theta_{2i} + i\cos\theta_{2r}\sinh\theta_{2i}) \quad (31)$$
$$= (n_{3r} + in_{3i})(\sin\theta_{3r}\cosh\theta_{3i} + i\cos\theta_{3r}\sinh\theta_{3i}).$$

which is a generalization of the usual Snell's law; the quantities $n_{1r}$, $n_{2r}$, $n_{2i}$, $n_{3r}$ and $n_{3i}$ are determined by Eqs. (19) and (20) so that the angle components are determined from Eqs. (31):

$$\sin\theta_{ar}\cos h\theta_{ai} = n_{1r}n_{ar}\sin\theta_1/(n_{ar}^2 + n_{ai}^2) \quad (a=2,3), \quad (32)$$

$$\cos\theta_{ar}\sin h\theta_{ai} = -n_{1r}n_{ai}\sin\theta_1/(n_{ar}^2 + n_{ai}^2). \quad (33)$$

For any incidence angle $\theta_1$ Eqs. (32) and (33) may be solved simultaneously for $\theta_{ar}$ and $\theta_{ai}$, viz.

$$\sin h^2\theta_{ai} = \tfrac{1}{2}\{1 - N^2w^2 + [(N^2w^2-1)^2 + 4n_{ai}^2w^2]^{\frac{1}{2}}\},$$

$$\cos^2\theta_{ar} = -(2)^{\frac{1}{2}}n_{ai}w/\{1 - N^2w^2 + [(N^2w^2-1)^2 + 4n_{ai}^2w^2]^{\frac{1}{2}}\},$$

$$N^2 = n_{ar}^2 + n_{ai}^2.$$

The solutions $E_{ao,r}'$, $E_{ao,i}'$, $E_{bo,r}$ and $E_{bo,i}$ of Eqs. (27)–(30) may be combined to produce the desired (complex) amplitude reflection and transmission coefficients in the following manner:

$$r_{12} = (E'_{10,r} + iE'_{10,i})/(E_{10,r} + iE_{10,i}) = \sum_{j=1}^{4}(\overline{M}_{j1} + i\overline{M}_{j2})F_j/(E_{10,r} + iE_{10,i}), \quad (34)$$

$$t_{21} = (E_{20,r} + iE_{20,i})/(E_{10,r} + iE_{10,i}) = \sum_{j=1}^{4}(\overline{M}_{j3} + i\overline{M}_{j4})F_j/(E_{10,r} + iE_{10,i}), \quad (35)$$

$$r_{21} = (E_{10,r} + iE_{10,i})/(E_{20,r} + iE_{20,i}) = \sum_{j=1}^{4}(\overline{N}_{j1} + i\overline{N}_{j2})G_j/(E_{20,r} + iE_{20,i}), \quad (36)$$

$$t_{21} = (E'_{20,r} + iE'_{20,i})/(E_{20,r} + iE_{20,i}) = \sum_{j=1}^{4}(\overline{N}_{j3} + i\overline{N}_{j4})G_j/(E_{20,r} + iE_{20,i}), \quad (37)$$

$$r_{23} = (E_{30,r} + iE_{30,i})/(E_{20,r} + iE_{20,i}) = \sum_{j=1}^{4}(\overline{O}_{j1} + i\overline{O}_{j2})H_j/(E_{20,r} + iE_{20,i}), \quad (38)$$

$$t_{23} = (E'_{20,r} + iE'_{20,i})/(E_{20,r} + iE_{20,i}) = \sum_{j=1}^{4}(\overline{O}_{j3} + i\overline{O}_{j4})H_j/(E_{20,r} + iE_{20,i}) \quad (39)$$

$$r_{32} = (E'_{30,r} + iE'_{30,i})/(E_{30,r} + iE_{30,i}) = \sum_{j=1}^{4}(\overline{P}_{j1} + i\overline{P}_{j2})J_j/(E_{30,r} + iE_{30,i}), \quad (40)$$

$$t_{32} = (E_{20,r} + iE_{20,i})/(E_{30,r} + iE_{30,i}) = \sum_{j=1}^{4}(\overline{P}_{j3} + i\overline{P}_{j4})J_j/(E_{30,r} + iE_{30,i}), \quad (41)$$

$$r_{31} = (E'_{30,r} + iE'_{30,i})/(E_{30,r} + iE_{30,i}) = \sum_{j=1}^{4}(\overline{Q}_{j1} + i\overline{Q}_{j2})K_j/(E_{30,r} + iE_{30,i}), \quad (42)$$

$$t_{31} = (E_{10,r} + iE_{10,i})/(E_{30,r} + iE_{30,i}) = \sum_{j=1}^{4}(\overline{Q}_{j3} + i\overline{Q}_{j4})K_j/(E_{30,r} + iE_{30,i}), \quad (43)$$

$$M = (M_{ij}) = \begin{bmatrix} cc_1 & ss_1 & -cc_2 & -ss_2 \\ -ss_1 & +cc_1 & +ss_2 & -cc_2 \\ -A_1 & B_1 & -A_2 & +B_2 \\ -B_1 & -A_1 & -B_2 & -A_2 \end{bmatrix}, \quad (44)$$

$$N = (N_{ij}) = \text{matrix } M \text{ with indices } (1,2) \rightarrow (2,1) \quad (45)$$

$$O = (O_{ij}) = \text{matrix } M \text{ with indices } (1,2) \rightarrow (2,3) \quad (46)$$

-continued $P = (P_{ij})$ = matrix $M$ with indices $(1,2) \to (3,2)$  (47)

$Q = (Q_{ij})$ = matrix $M$ with indices $(1,2) \to (3,1)$  (48)

$cc_a = \cos\theta_{ar}\cosh\theta_{ai}, (a = 1,2,3)$  (49)

$ss_a = \sin\theta_{ar}\sinh\theta_{ai},$  (50)

$cs_a = \cos\theta_{ar}\sinh\theta_{ai},$  (51)

$sc_a = \sin\theta_{ar}\cosh\theta_{ai},$  (52)

$A_a = \epsilon_a sc_a - (4\pi\sigma_a/\omega) cs_a, (\sigma_1 = 0)$  (53)

$B_a = \epsilon_a cs_a + (4\pi\sigma_a/\omega) sc_a,$  (54)

$\overline{M}_{ij} = \frac{\partial}{\partial M_{ij}} \ln [\det(M)],$  (55)

$\overline{N}_{ij} = \frac{\partial}{\partial N_{ij}} \ln [\det(N)],$  (56)

$\overline{O}_{ij} = \frac{\partial}{\partial O_{ij}} \ln [\det(O)],$  (57)

$\overline{P}_{ij} = \frac{\partial}{\partial P_{ij}} \ln [\det(P)],$  (58)

$\overline{Q}_{ij} = \frac{\partial}{\partial Q_{ij}} \ln [\det(Q)],$  (59)

$F_1 = -E_{10,r}cc_1 - E_{10,i}ss_1,$  (60)

$F_2 = -E_{10,r}ss_1 - E_{10,i}cc_1,$  (61)

$F_3 = -E_{10,r}[\epsilon_1 sc_1 - (4\pi\sigma_1/\omega) cs_1] + E_{10,i}[\epsilon_1 cs_1 + (4\pi\sigma_1/\omega) sc_1],$  (62)

$F_4 = -E_{10,r}[\epsilon_1 cs_1 + (4\pi\sigma_1/\omega) sc_1] - E_{10,i}[\epsilon_1 sc_1 - (4\pi\sigma_1/\omega) cs_1],$  (63)

$G_j = F_j$ with indices $(1,2) \to (2,1)$  (64)

$H_j = F_j$ with indices $(1,2) \to (2,3)$  (65)

$J_j = F_j$ with indices $(1,2) \to (3,2)$ $K_j = F_j$ with indices $(1,2) \to (3,1)$ Here, det(D) denotes the determinant of the 4×4 matrix D(=M,N,O,P or Q). The electric field $E_{ao,r}+iE_{ao,i}$ in the denominator in each of the Eqs. (34)–(43) represents the amplitude of the electromagnetic wave incident upon the (a,b) interface. The method for determination of the amplitude reflection and transmission coefficients $r_{ij}$ and $t_{ij}$ set forth in Eqs. (24)–(67) uses the boundary continuity equations (23); and this method will therefore be called the Boundary Continuity Method herein.

Interest centers here, not on the amplitude of reflection and transmission coefficients, but on the measurable reflectivity R and transmission T. For purposes of subsequent analysis write $$r_{ij} = \hat{r}_{ij}e^{i\theta_{ij}}, \quad (i,j = 1,2,3),$$
$$t_{ij} = \hat{t}_{ij}e^{i\psi_{ij}},$$  (68)

where $\hat{r}_{ij}, \hat{t}_{ij}, \theta_{ij}$ and $\psi_{ij}$ are real quantities. Using Eqs. (68), the reflectivity at the (1,2) interface becomes $$R = \left| r_{12} + \frac{t_{12}r_{23}t_{21}\exp(iq_{2r}L_2\eta_2)\exp(\alpha_2 L_2)}{1 - r_{21}r_{23}\exp(iq_{2r}L\eta)\exp(\alpha_2 L_2)} \right|^2$$  (66)

$$= \{\hat{r}_{12}^2 + 2[-\hat{r}_{12}^2\hat{r}_{21}\hat{r}_{23}\cos(q_{2r}L_2\eta_2 + \theta_{21} + \theta_{23}) + \hat{r}_{12}\hat{r}_{23}\hat{t}_{12}\hat{t}_{21}\cos(q_{2r}L_2\eta_2 - \theta_{12} + \theta_{23} + \psi_{12} + \psi_{21})] e^{-\alpha_2 L_2} +$$
$$[\hat{r}_{12}^2\hat{r}_{21}^2\hat{r}_{23}^2 + \hat{r}_{23}^2\hat{t}_{12}^2\hat{t}_{21}^2 - 2\hat{t}_{12}\hat{r}_{21}\hat{r}_{23}^2\hat{t}_{12}\hat{t}_{21}\cos(\theta_{12} + \theta_{21} - \psi_{12} - \psi_{21})] e^{-2\alpha_2 L_2}\}/\{1 - 2\hat{r}_{12}\hat{r}_{23}\cos{\rm INAREA}$$ (67) (69)

$q_{2r}L_2\eta_2 + \theta_{21} + \theta_{23}) e^{-\alpha_2 L_2} +$ $\hat{r}_{21}^2\hat{r}_{23}^2\} e^{-2\alpha_2 L_2}$ $L_2 = 2t_2\sec\theta_{2r},$  (70)

$\eta_2 = 1 - \sin\theta_1\sin\theta_{2r}/n_{2r}.$  (71)

This again yields a quadratic equation for the unknown transparency $\exp(-\alpha_2 L_2)$ that is easily solved, viz.

$$\exp(-\alpha_2 L_2) = [u \pm (u^2 - tv)^{\frac{1}{2}}]/t$$  (72)

$$t = R\hat{r}_{21}^2\hat{r}_{23}^2 - \hat{r}_{12}^2\hat{r}_{21}^2\hat{r}_{23}^2 - \hat{r}_{23}^2\hat{t}_{12}^2\hat{t}_{21}^2 + 2\hat{r}_{12}\hat{r}_{21}\hat{r}_{23}^2\hat{t}_{12}\hat{t}_{21}\cos(\theta_{12} + \theta_{21} - \psi_{12} - \psi_{21}),$$  (73)

-continued $$u = R\hat{r}_{12}\hat{r}_{23}\cos(q_{2r}L_2\eta_2 + \theta_{21} + \theta_{23}) - \quad (74)$$
$$\hat{r}_{12}^2\hat{r}_{21}\hat{r}_{23}\cos(q_{2r}L_2\eta_2 + \theta_{21} + \theta_{23}) +$$
$$\hat{r}_{12}\hat{r}_{23}\hat{t}_{12}\hat{t}_{21}\cos(q_{2r}L_2\eta_2 - \theta_{12} + \theta_{23} + \psi_{12} + \psi_{21}),$$

$$v = R - \hat{r}_{12}^2. \quad (75)$$

The relation (72) replaces the simpler relation (8) for the determination of transparency $\exp(-\alpha_2 L_2)$ from a measurement of reflectivity R and knowledge of the complex coefficients $r_{ij}$ and $t_{ij}$. Although the expression for film transparency $\exp(-\alpha_2 L_2)$ found in Eq. (72) is formally more correct than is Eq. (8) for an absorbing film, for very high frequencies (for which $\pi\sigma_2/\epsilon_2\omega << 1$), the simpler expression in Eq. (8) may provide sufficient accuracy in many situations.

The expressions in Eqs. (24)–(67) are appropriate for a p-polarized incident wave, as indicated in FIG. 8. The expressions for an s-polarized incident wave are analogous.

When an absorbing medium is present, the usual notion of Brewster's angle as the angle of incidence $\theta_1$ for which $r_{12,p}$ vanishes is no longer satisfied. The amplitude reflection coefficient $r_{12,p}$ is now a complex quantity that varies with $\theta_1$, and the real and imaginary components of $r_{12,p}$ will not vanish simultaneously. From the formalism developed in Eqs. (24)–(67) at the (1,2) interface with $\theta_{1i}=\sigma_1=0$ one finds $x_2=4\pi\sigma_2/\omega$.

$$Re(r_{12,p}) = \{(\epsilon_2^2 - x_2^2)\cos^2\theta_1((cs_2)^2 - (sc_2)^2) + \quad (76)$$
$$4\epsilon_2 x_2\cos^2\theta_1(cc_2)(ss_2) - \epsilon_1^2\sin^2\theta_1((cc_2)^2 + (ss_2)^2)\}/$$
$$[(\epsilon_2^2 + x_2^2)\cos^2\theta_1((sc_2)^2 + (cs_2)^2) + \epsilon_1^2\sin^2\theta_1((cc_2)^2 + (ss_2)^2) +$$
$$\tfrac{1}{2}\epsilon_1\epsilon_2\sin 2\theta_1\sin 2\theta_{2r} - \tfrac{1}{2}(\epsilon_1 x_2\sin 2\theta_1\sinh 2\theta_{2i}],$$

$$Im(r_{12,p}) = -\tfrac{1}{2}\epsilon_2\sin 2\theta_1[\epsilon_2\sinh 2\theta_{2i} + x_2\sin 2\theta_{2r}]/ \quad (77)$$
$$[(\epsilon_2^2 + x_2^2)\cos^2\theta_1((sc_2)^2 + (cs_2)^2) + \epsilon_1^2\sin^2\theta_1((cc_2)^2 + (ss_2)^2) +$$
$$\tfrac{1}{2}\epsilon_1\epsilon_2\sin 2\theta_1\sin 2\theta_{2r} - \tfrac{1}{2}(\epsilon_1 x_2\sin 2\theta_1\sinh 2\theta_{2i}],$$

The denominator for each of $Re(r_{12,p})$ and $Im(r_{12,p})$ is positive, and it is easily verified that the numerators for each of these two quantities change sign at least once as $\theta_1$ increases from 0 to $\pi/2$, with $\theta_{2i}<0$.

The effective Brewster's angle for this situation may be defined by $$\frac{\partial}{\partial\theta_1}\{Re(r_{12,p})^2 + Im(r_{12,p})^2\}_{\theta'_{1B}} = 0, \quad (78)$$

$$|r_{12,p}| = \text{minimum}.$$

An alternative definition with a different numerical result is $$Re(r_{12,p})_{\theta_1=\theta_{1B'}}=0. \quad (79)$$

An observed above, $Re(r_{12,p})$ and $Im(r_{12,p})$ do not, in general, vanish simultaneously; and only the effects of the quantities $\hat{r}_{12,p}=|r_{12,p}|$ and the complex phase angle $\exp(i\theta_{12})=r_{12,p}/|r_{12,p}|$ are observable, through measurement of quantities such as R in Eq. (69). Thus, the Brewster's angle $\theta_{1B}'$ (re)definition set forth in Eq. (78) is more satisfactory here. Because $|r_{12,p}|$ will not, in general, vanish for any realistic value of incidence angle $\theta_1$, the earlier-discussed theoretical difficulty in measurement of R (for non-absorbing media) does not occur. However, the value of $|r_{12,p}|$ at the new Brewster's angle $\theta_{1B}'$ may be very small, and the earlier-discussed two-angle measurement of R near $\theta_1=\theta_{1B}'$ may still be useful for absorbing media.

Absorption measurements of the photoresist film mounted on a substrate can also be made by use of light transmission, if the thickness of substrate is not substantially opaque at the measurement wavelength. Here, it is preferable to use substantially normal incidence ($\theta_1\cong 0$), although nonzero incidence angles may also be used. By another extension of the argument used to derive Eq. (7) for reflectivity R, the transmission of the film-substrate configuration in the presence of film absorption ($\alpha_2$) and substrate absorption ($\alpha_3$) absorption is found from FIG. 9 to be $$T=I_t/I_0=(1-r_{12}^2)(1-r_{23}^2)(1-r_{31}^2) \quad (80)$$
$$e^{-2(\alpha_2 L_2+\alpha_3 L_3)}/[(1-2r_{23}r_{21}(e^{-2\alpha_2 L_2})\cos\beta_2+r_{23}^2 r_{21}^2 e^{-4\alpha_2 L_2})(1-2r_{31}r_{32}e^{-2\alpha_3 L_3}\cos\beta_3+r_{31}^2 r_{32}^2 e^{-4\alpha_3 L_3})]$$

Figure 9:
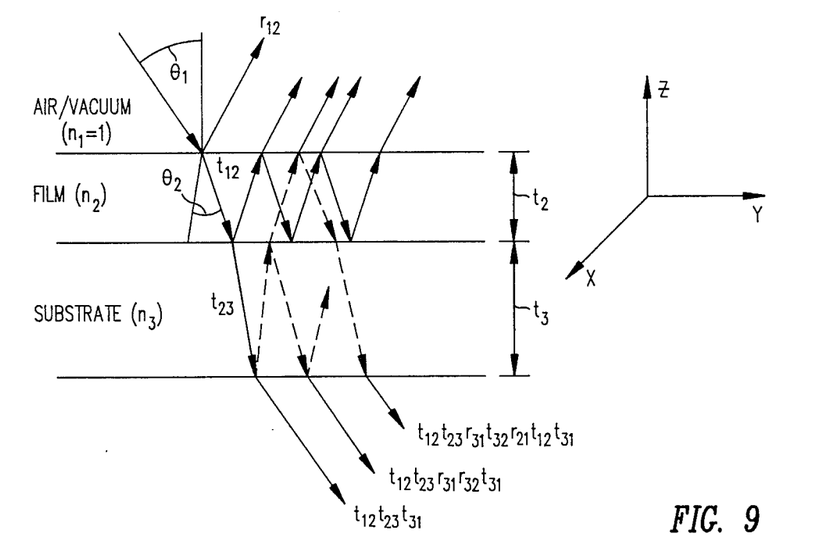
FIG. 9 is a schematic view of the film-substrate combination and the various reflected and transmitted amplitude components that contribute to measured transmission T.

$I_o$=incident intensity,
$I_t$=transmitted intensity, $$\beta_2 = \frac{4\pi n_2 t_2}{\lambda}\cos\theta_2,$$

$$\beta_3 = \frac{4\pi n_3 t_3}{\lambda}\cos\theta_3,$$

$L_2=t_2\sec\theta_2$=single pass optical path length in film,
$L_3=t_3\sec\theta_3$=single pass optical path length in substrate, $$r_{31,p}(\theta_1) = \frac{n_1\cos\theta_3 - n_3\cos\theta_1}{n_1\cos\theta_3 + n_3\cos\theta_1}, \quad (81)$$

$$r_{31,s}(\theta_1) = \frac{n_3\cos\theta_3 - n_1\cos\theta_1}{n_3\cos\theta_3 + n_1\cos\theta_1}, \quad (82)$$

where the other quantities may be determined from Eqs. (2)–(6). T is assumed to be measured with the configuration shown in FIG. 8. If the substrate thickness and material characteristics (specifically, $\alpha_3$) and geometric parameters are accurately known, the transmission equation (18) for T may be rearranged to yield a solution for the absorption $a=1-e^{-\alpha_2 L_2}$, with $$e^{-2\alpha_2 L_2} = \{(r_{21}r_{23}\cos\beta_2 + 1/FT) \pm [(r_{21}r_{23}\cos\beta_2 + 1/FT)^2 \quad (83)$$
$$- r_{21}^2 r_{23}^2]^{\tfrac{1}{2}}\}/r_{21}^2 r_{23}^2,$$

$$\frac{F}{2} = \quad (84)$$

$$\frac{(1 - 2r_{31}r_{32}(e^{-2\alpha_3 L_3})\cos\beta_2 + r_{31}^2 r_{32e}^2 -4\alpha_3 L_3)e^{2\alpha_3 L_3}}{(1-r_{12}^2)(1-r_{23}^2)(1-r_{31}^2)} \quad (\geq 0).$$

For the choice $\theta_1=\theta_{B1}=\tan^{-1}(n_2)$, $r_{12}=r_{21}=0$ for p-polarized incident light, Eq. (85) reduces to $$e^{-2\alpha_2 L_2}=TF/2. \quad (85)$$

The choice $\theta_1=\sin^{-1}[n_2 n_3/(n_2^2+n_3^2)^{\tfrac{1}{2}}]$ for which $\theta_2=\theta_{2B}$, or $\theta_1=\sin^{-1}[n_3/(1+n_3^2)^{\tfrac{1}{2}}]$ for which $\theta_3=\theta_{3B}=\tan^{-1}(1/n_3)$, results in no substantial simplification of Eqs. (80) or (83).

In a similar manner, by analogy with the development of the expressions (69)–(75) for reflectivity, the transmission for an absorbing film and absorbing substrate becomes $$T = \hat{r}_{12}^2 \hat{r}_{23}^2 \hat{r}_{31}^2 \exp[-2\alpha_2 L_2 - 2\alpha_3 L_3]/\{[1 - 2\hat{r}_{21}\hat{r}_{23}\cos(q_{2r}L_2\eta_2 \quad (86)$$
$$+ \theta_{21} + \theta_{23}) e^{-2\alpha_2 L_2} + \hat{r}_{21}^2 \hat{r}_{23}^2 e^{-4\alpha_2 L_2}] [1 - 2\hat{r}_{31}\hat{r}_{32}\cos(q_{3r}L_3\eta_3 +$$
$$\theta_{31} + \theta_{32}) e^{-2\alpha_3 L_3} + \hat{r}_{31}^2 \hat{r}_{32}^2 e]^{2\alpha_3 L_3}]\},$$

$$L_3 = 2h_3 \sec\theta_{3r}, \quad (87)$$

$$\eta_3 = 1 - \sin\theta_1 \sin\theta_{3r}/n_{3r}. \quad (88)$$

This yields, for the transparency, $$(1 - a)^2 = e^{-2\alpha_2 L_2} = [u' \pm (u'^2 - t'v')^{\frac{1}{2}}]/t', \quad (89)$$

$$t' = \hat{r}_{21}^2 \hat{r}_{23}^2 \quad (90)$$

$$u' = r_{21}r_{23}\cos(q_{2r}L_2\eta_2 + \theta_{21} + \theta_{23}) + 1/FT, \quad (91)$$

$$v' = 1, \quad (92)$$

$$F/2 = [e^{2\alpha_3 L_3} - 2\hat{r}_{31}\hat{r}_{32}\cos(q_{3r}L_3\eta_3 + \theta_{31} + \theta_{32}) + \quad (93)$$
$$\hat{r}_{31}^2 \hat{r}_{32}^2 e^{-2\alpha_2 L_2}]/\hat{r}_{12}^2 \hat{r}_{23}^2 \hat{r}_{31}^2.$$

The wavelength for the incident light may be in-band ($\lambda \approx 300$–$450$ nm) or out-of-band. For an in-band wavelength, a silicon substrate is substantially opaque ($e^{-\alpha_3 L_3} \doteq 0$) and a measurement of T is difficult for such a substrate. If the substrate is changed to a relatively transparent material such as glass ($n_3 \doteq 1.5$) or plastic, the measurement of T may be made and Eq. (21) may be used to determine $\alpha_2$.

Figure 11:
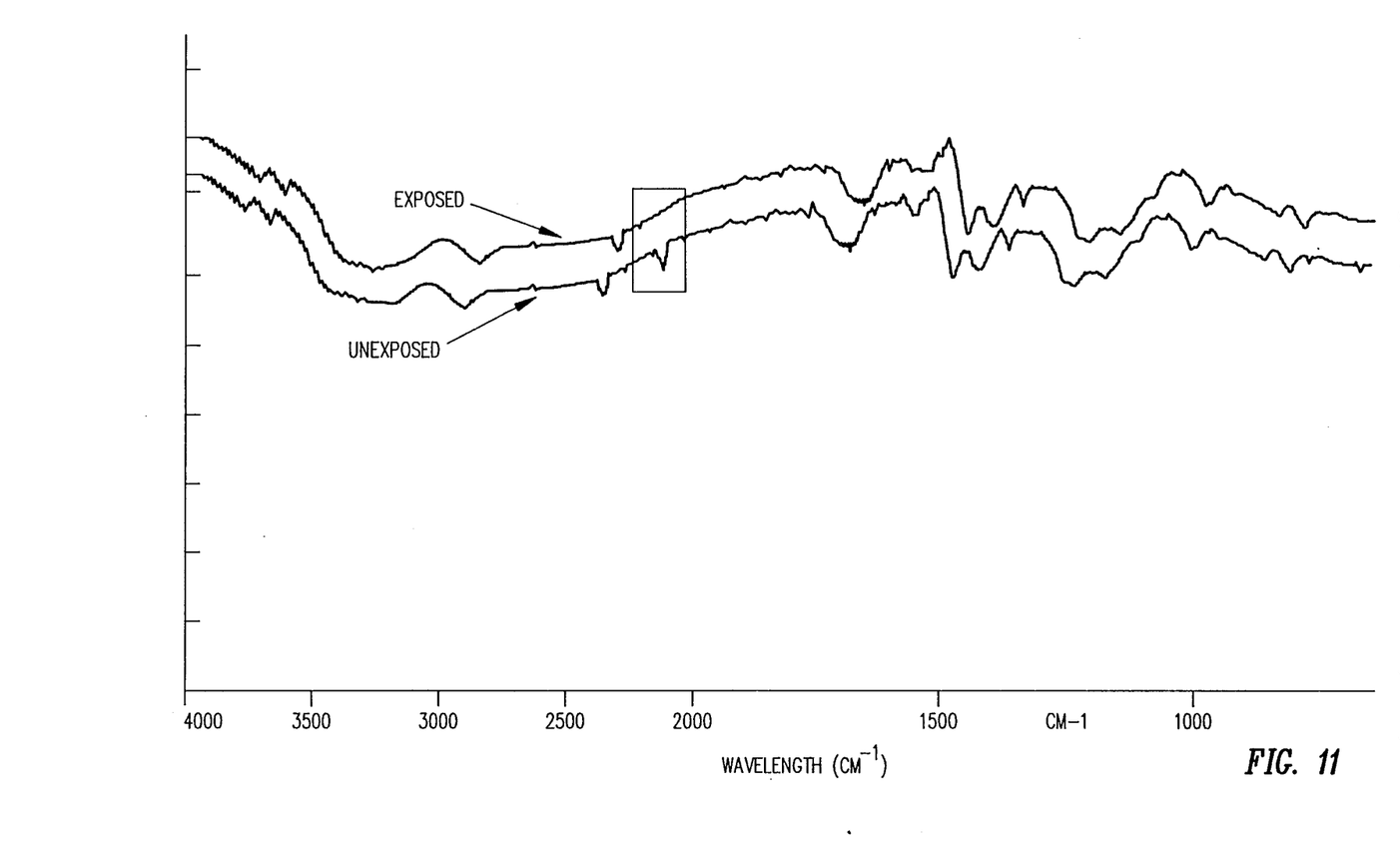
FIG. 11 is a graphic view of the infrared absorption of AZ 4110 photoresist material for the wavelength number range 1000 cm$^{-1} < \lambda < 4000$ cm$^{-1}$ (wavelength range 2.5 $\mu$m $< \lambda < 10$ $\mu$m).

When an out-of-band wavelength ($\lambda << 300$ nm or $\lambda >> 450$ nm) is to be used, one attractive choice is $\lambda \approx 4.7$ μm, where silicon is relatively transparent but the (exposed) photosensitive component manifests infrared absorption at approximately 2100 cm$^{-1}$. At $\lambda = 4.7$ μm silicon is relatively transparent (see FIG. 11), but its high refractive index ($n_3 \approx 3.3$) produces strong reflection at normal incidence at the film-substrate interface ($r_{23} \approx 0.34$) and at the substrate-vacuum interface ($r_{31} \approx -0.54$), if the rear surface is flat and polished. At long wavelengths such as $\lambda = 4.7$ μm, the effect on transmission T of a change in film thickness is relatively small, which is another attractive feature of use of long wavelengths.

Although this discussion has focused on Si or glass as the substrate material, other solid semiconductor materials such as Ge, GaP, GaAs, GaSb, GaAs$_x$P$_{1-x}$, InP, InAs, InSb, and InAs$_x$P$_{1-x}$ may also be used as the substrate material. The dielectric functions and optical parameters of most of these materials have been reviewed by Aspnes and Studna in "Dielectric Functions and Optical Parameters of Si, Ge, GaP, GaAs, GaSb, InP, InAs, and InSb from 1.5 to 6.0 eV," Physical Review B, Vol. 27 (1983) 985-1009. Each of the above-listed materials has its own optical window regions and opaque regions (where the imaginary component $n_i$ of the complex refractive index $n = n_r + in_i$ is substantially different from zero).

For Si, for example, according to the results of Aspnes and Studna, $n_i < 0.1$ (substantially transparent) for wavelength $\lambda \geq 0.48$ μm and $n_i$ tends slowly to zero as $\lambda$ increases beyond this point; but Si is substantially opaque for $\lambda < 0.38$ μm. The material Ge is substantially opaque for $\lambda < 0.61$ μm. The material GaP is substantially transparent for $\lambda > 0.44$ μm and is substantially opaque for $\lambda < 0.35$ μm. The material GaAs is substantially transparent for $\lambda > 0.76$ μm and is substantially opaque for $\lambda < 0.44$ μm. The material GaSb is substantially opaque for $\lambda < 0.64$ μm, although it apparently becomes transparent, if at all, only for $\lambda > 0.82$ μm. The material InP is substantially opaque for $\lambda < 0.43$ μm and apparently becomes transparent, if at all, only for $\lambda > 0.82$ μm. The material InAs is substantially opaque for $\lambda < 0.54$ μm. The material InSb is substantially opaque at all wavelengths $\lambda < 0.73$ μm. Similarly, Na-based glass, P-based glass, B-based glass, etc. have different transparent and opaque regions. For reflectivity measurements, one's choice of substrate material and/or wavelength is probably unrestricted, unless the substrate thickness is sufficiently thin that unwanted returning signals, reflected from the substrate rear face, are present. For the transmission measurements, however, one must choose the substrate material and/or wavelength carefully to avoid or suppress the absorption that is naturally present in the substrate.

Although the preferred embodiments of the invention have been shown and described herein, modification thereof can be made without departing from the scope of the invention.

We claim:

1. A method for determining the absorption $a = 1 - e^{-\alpha_2 L_2}$ corresponding to propagation of light of a predetermined wavelength $\lambda$ linearly through a predetermined first material of path length $L_2$, where $\alpha_2$ is the linear absorption parameter of this first material, where a substantially planar film of refractive index $n_2(\lambda)$ of this first material of predetermined thickness $t_2$ is mounted on a substrate layer of a second predetermined material having refractive index $n_3(\lambda)$, the method comprising the steps of:

providing a source of light of wavelength $\lambda$;

positioning the film-substrate combination so that the film lies between at least a portion of the substrate and the light source;

propagating an incident beam of the light in a vacuum or in air from the light source toward the exposed face of the film at a predetermined incidence angle of $\theta_1$;

allowing the light beam to be reflected at the exposed face of the film and at the interface between film and substrate and measuring the total reflectivity $R = I_r/I_0$ of this light beam from the film-substrate combination, where $I_0$ is the intensity of the incident light beam and $I_r$ is the measured intensity of the reflected light beam; and determining the absorption a substantially from the expressions $$1 - a = \left\{ \left[ -r_{12}(1 - R)\cos\left(\frac{4\pi n_2 t_2}{\lambda}\cos\theta_2\right) \pm \right. \right.$$
$$\left[ \hat{r}_{12}^2 (1 - R)^2 \cos^2\left(\frac{4\pi n_2 t_2}{\lambda}\cos\theta_2\right) + \right.$$
$$\left. \left. (R - \hat{r}_{12}^2)(1 - R\hat{r}_{12}^2) \right]^{\frac{1}{2}} \right] / r_{23}(1 - R\hat{r}_{12}^2) \right\},$$

$$\cos\theta_2 = \sqrt{1 - \sin^2\theta_1/n_2^2},$$

-continued $$\cos\theta_3 = \sqrt{1 - \sin\theta_1^2/n_3^2},$$

and where $r_{12}=r_{12,k}(\theta_1, \theta_2)$ and $r_{23}=r_{23,k}(\theta_2, \theta_3)$ are, respectively, the amplitude reflection coefficients appropriate for the vacuum-film interface at incidence angle $\theta_1$ in the vacuum and for the film-substrate interface at incidence angle $\theta_2$ in the film and $k(=p$ or $s)$ is the polarized index corresponding to the incident beam.

2. The method according to claim 1, including the further step of choosing said angle of incidence as substantially $\theta_1=\tan^{-1}(n_2)$ and choosing p-polarized light with said polarization index $k=p$ for said light beam.

3. The method according to claim 1, including the further step of choosing said wavelength $\lambda$ of said light beam substantially in the range 300 nm$\leq\lambda\leq$450 nm.

4. The method according to claim 1, including the further steps of choosing said substrate material as Si and choosing said wavelength of said light beam as substantially $\lambda=4.7$ $\mu$m.

5. The method according to claim 1, including the further step of choosing said substrate material from the class of solid materials that are at least partly transparent in a portion of the visible and infrared wavelength spectrum and consisting of glass, Si, Ge, GaP, GaAs, $GaAs_xP_{1-x}$, GaSb, InP, InAs, $InAs_xP_{1-x}$ and InSb.

6. A method according to claim 1, further including the steps of:
choosing said predetermined incidence angle $\theta_1$ in the range $\theta_{1B}<\theta_1\leq\theta_{1B}+\Delta_1$, where $\theta_{1B}=\tan^{-1}(n_2(\lambda))$ and $\Delta_1$ is a predetermined small angle of the order of a few degrees;
choosing a second predetermined incidence angle $\theta_1'$ in the range $\theta_{1B}-\Delta_1\leq\theta_1'\theta_{1B}$; and
repeating the steps of claim 1, with the incidence angle $\theta_1'$ replacing said incidence angle $\theta_1$.

7. A method for determining the absorption $a=1-=e^{-\alpha_2 L_2}$ corresponding to propagation of light of a predetermined wavelength $\lambda$ linearly through a predetermined first material of path length $L_2$, where $\alpha_2$ is the linear absorption parameter of this first material, where a substantially planar film of complex refractive index $n_2=n_{2r}(\lambda)+in_{2i}(\lambda)$ ($i^2=-1$) of this first material of predetermined thickness $t_2$ is mounted on a substrate layer of a second predetermined material having refractive index $n_3=n_{3r}(\lambda)+in_{3i}(\lambda)$ (where $n_{3i}(\lambda)$ may be zero), the method comprising the steps of:
providing a source of light of wavelength $\lambda$;
positioning the film-substrate combination so that the film lies between at least a portion of the substrate and the light source;
propagating a p-polarized incident beam of the light in a vacuum or in air from the light source toward the exposed face of the film at a predetermined incidence angle of $\theta_1$;
allowing the light beam to be reflected at the exposed face of the film and at the interface between film and substrate and measuring the total reflectivity $R=I_r/I_o$ of this light beam from the film-substrate combination, where $I_o$ is the intensity of the incident light beam and $I_r$ is the measured intensity of the reflected light beam; and
determining the absorption $a$ substantially from the expressions $$1 - a = [u \pm (u^2 - tv)^{\frac{1}{2}}]/t$$

$$t = R\hat{r}_{12}^2\hat{r}_{23}^2 - \hat{r}_{12}^2\hat{r}_{21}^2\hat{r}_{23}^2 - \hat{r}_{23}^2\hat{t}_{12}^2\hat{t}_{21}^2 +$$
$$2\hat{r}_{12}\hat{r}_{21}\hat{r}_{23}^2\hat{t}_{12}\hat{t}_{21}\cos(\theta_{12} + \theta_{21} - \psi_{12} - \psi_{21}).$$

$$u = R\hat{r}_{21}\hat{r}_{23}\cos(q_{2r}L_2\eta_2 + \theta_{21} + \theta_{23}) -$$
$$\hat{r}_{12}^2\hat{r}_{21}\hat{r}_{23}\cos(q_{2r}L_2\eta + \theta_{21} + \theta_{23}) +$$
$$\hat{r}_{12}\hat{r}_{23}\hat{t}_{12}\hat{t}_{21}\cos(q_{2r}L_2\eta_2 - \theta_{12} + \theta_{23} + \psi_{12} + \psi_{21}),$$

$$v = R - \hat{r}_{12}^2,$$
$$\eta_2 = 1 - \sin\theta_1\sin\theta_{3r}/n_{3r},$$
$$r_{ij} = |r_{ij}|, (i,j = 1,2,3),$$
$$t_{ij} = |t_{ij}|,$$
$$\theta_{ij} = \tan^{-1}[Im(r_{ij})/Re(r_{ij})],$$
$$\psi_{ij} = \tan^{-1}[Im(t_{ij})/Re(t_{ij})],$$

where the complex numbers $r_{ij}$ and $t_{ij}$ are amplitude reflection and transmission coefficients and are determined from the boundary continuity method.

8. The method according to claim 7, including the further step of choosing said angle of incidence $\theta_1$ in the interval $(0,\pi/2)$ as substantially a solution of the equation $$Re(r_{12})^2 + Im(r_{12})^2 = \text{minimum}.$$

9. The method according to claim 7, including the further step of choosing said wavelength $\lambda$ of said light beam substantially in the range 300 nm$\leq\lambda\leq$450 nm.

10. The method according to claim 7, including the further steps of choosing said substrate material as Si and choosing said wavelength $\lambda$ of said light beam as substantially $\lambda=4.7$ $\mu$m.

11. The method of claim 7, including the further step of choosing said substrate material from the class of solid materials that are at least partly transparent in a portion of the visible and infrared wavelength spectrum and consisting of glass, Si, Ge, GaP, GaAs, $GaAs_xP_{1-x}$, GaSb, InP, InAs, $InAs_xP_{1-x}$ and InSb.

12. A method for determining the absorption $a=1--e^{-\alpha_2 L_2}$ corresponding to propagation of light of a predetermined wavelength $\lambda$ linearly through a predetermined first material of path length $L_2$, where $\alpha_2$ is the linear absorption parameter of this first material, where a substantially planar film of refractive index $n_2(\lambda)$ of this first material of predetermined thickness $t_2$ is mounted on a substrate layer of a second predetermined material having predetermined thickness $t_3$, refractive index $n_3(\lambda)$ and known linear absorption parameter $\alpha_3$, the method comprising the steps of:
providing a source of light of wavelength $\lambda$;
positioning the film-substrate combination so that the film lies between at least a portion of the substrate and the light source;
propagating an incident beam of the light in a vacuum or in air from the light source toward the exposed face of the film at a predetermined incidence angle $\theta_1(0\leq\theta_1<\pi/2)$;
allowing the light beam to be transmitted through the film and substrate and measuring the total transmission $T=I_t/I_o$ of this light beam from the film-substrate combination, where $I_o$ is the intensity of the incident light beam and $I_t$ is the measured intensity of the transmitted light beam; and
determining the absorption $a$ substantially from the expressions $$(1-a)^2 = \{[(r_{21}r_{23}\cos\beta_2 + 1/TF)^2 - r_{21}^2 r_{23}^2]^{\frac{1}{2}} +$$
$$(r_{21}r_{23}\cos\beta_2 + 1/TF)\}/r_{21}^2 r_{23}^2,$$

$$F/2 = \frac{(e^{\alpha_2 L_2} - 2r_{31}r_{32}\cos\beta_3 + r_{31}^2 r_{32}^2 e^{-2\alpha_3 L})}{(1-r_{12}^2)(1-r_{23}^2)(1-r_{31}^2)},$$

$$\beta_2 = \frac{4\pi n_2 t_2}{\lambda}\cos\theta_2,$$

$$\beta_3 = \frac{4\pi n_3 t_3}{\lambda}\cos\theta_3,$$

$$L_2 = t_2 \sec\theta_2,$$

$$L_3 = t_3 \sec\theta_3,$$

$$\cos\theta_2 = [1-\sin^2\theta_1/n_2^2]^{\frac{1}{2}},$$

$$\cos\theta_3 = [1-\sin^2\theta_1/n_3^2]^{\frac{1}{2}},$$

and where $r_{12} = r_{12,k}(\theta_1, \theta_2)$, $r_{23} = r_{23,k}(\theta_2, \theta_3)$ and $r_{31} = r_{31,k}(\theta_3, \theta_1)$ are the amplitude reflection coefficients appropriate for the vacuum-film interface at incidence angle $\theta_1$ in the vacuum, for the film-substrate interface at incidence angle $\theta_2$ in the film, and for the substrate-air interface at incidence angle $\theta_3$ within the substrate, and $k(=p$ or $s)$ is the polarization index corresponding to the incident beam.

13. The method according to claim 12, including the further steps of choosing said angle of incidence as substantially $\theta_1 = \tan^{-1}(n_2)$ and using p-polarized light with said polarization index $k=p$ for said light beam.

14. The method according to claim 12, including the further steps of choosing said substrate material as Si and choosing said wavelength $\lambda$ of said light beam as substantially $\lambda = 4.7 \mu m$.

15. The method according to claim 12, including the further step of choosing said substrate material from the class of solid materials that are at least partly transparent in a portion of the visible and infrared wavelength spectrum and consisting of glass, Si, Ge, GaP, GaAs, GaAs$_x$P$_{1-x}$, GaSb, InP, InAs, InAs$_x$P$_{1-x}$ and InSb.

16. A method for determining the absorption $a = 1 - e^{-\alpha_2 L_2}$ corresponding to propagation of light of a predetermined wavelength $\lambda$ linearly through a predetermined first material of path length $L_2$, where $\alpha_2$ is the linear absorption parameter of this first material, where a substantially planar film of complex refractive index $n_2 = n_{2r}(\lambda) + in_{2i}(\lambda)$ ($i = -1$) of this first material of predetermined thickness $t_2$ is mounted on a layer of a second predetermined material having refractive index $n_3 = n_{3r}(\lambda) + in_{3i}(\lambda)$ (where $n_{3i}(\lambda)$ may be zero), the method comprising the steps of:

providing a source of light of wavelength $\lambda$;

positioning the film-substrate combination so that the film lies between at least a portion of the substrate and the light source;

propagating a p-polarized incident beam of the light in a vacuum or in air from the light source toward the exposed face of the film at a predetermined incidence angle $\theta_1$ ($0 \leq \theta_1 < \pi/2$);

allowing the light beam to be transmitted through the film and substrate and measuring the total transmission $T = I_t/I_0$ of this light beam from the film-substrate combination, where $I_0$ is the intensity of the incident light beam and $I_t$ is the measured intensity of the reflected light beam; and determining the absorption a substantially from the expressions $$(1-a)^2 = e^{-2\alpha_2 L_2} = [u' \pm (u'^2 - t'v')^{\frac{1}{2}}]/t',$$

$t' = \hat{r}_{21}^2 \hat{r}_{23}^2$,
$u' = r_{21}r_{23}\cos(q_{2r}L_2\eta_2 + \theta_{21} + \theta_{23}) + 1FT$,
$v' = 1$ $F/2 = [e^{2\alpha_3 L_3} - 2\hat{r}_{31}\hat{r}_{32}\cos(q_{3r}L_3\eta_3 + \theta_{31} + \theta_{32}) + \hat{r}_{31}^2\hat{r}_{32}^2 e^{-2\alpha_3 L_3}]/\hat{r}_{12}^2\hat{r}_{23}^2\hat{r}_{31}^2,$ p1 $L_2 = t_2 \sec\theta_{2r}$,
$L_3 = t_3 \sec\theta_{3r}$,
$q_{2r} = (\omega/c)n_{2r}$,
$q_{3r} = (\omega/c)n_{3r}$,
$\eta_2 = 1 - \sin\theta_1 \sin\theta_{2r}/n_{2r}$,
$\eta_3 = 1 - \sin\theta_1 \sin\theta_{3r}/n_{3r}$,
$|r_{ij}| = \hat{r}_{ij}$, $(i,j = 1,2,3)$,
$|t_{ij}| = \hat{t}_{ij}$,
$\theta_{ij} = \tan^{-1}[\text{Im}(r_{ij})/\text{Re}(r_{im})]$,
$\psi_{ij} = \tan^{-1}[\text{Im}(t_{ij})/\text{Re}(t_{ij})]$, where the complex numbers $r_{ij}$ and $t_{ij}$ are the amplitude reflection and transmission coefficients and are determined from the boundary continuity method.

17. The method according to claim 17, including the further step of choosing said wavelength $\lambda$ of said light beam substantially in the range 300 nm $\leq \lambda \leq$ 450 nm.

18. The method according to claim 16, including the further steps of choosing said substrate material as Si and choosing said wavelength $\lambda$ of said light beam as substantially $\lambda = 4.7 \mu m$.

19. The method according to claim 16, including the further step of choosing said substrate material from the class of solid materials that are at least partly transparent in a portion of the visible and infrared wavelength spectrum and consisting of glass, Si, Ge, GaP, GaAs, GaAs$_x$P$_{1-x}$, GaSb, InP, InAs, InAs$_x$P$_{1-x}$ and InSb.

* * * * *